(12) United States Patent
Luechtenborg et al.

(10) Patent No.: US 9,018,593 B2
(45) Date of Patent: Apr. 28, 2015

(54) IRRADIATION METHOD AND DEVICE FOR CARRYING OUT THE METHOD

(75) Inventors: Robert Luechtenborg, Darmstadt (DE); Christoph Bert, Aschaffenburg (DE); Daniel Richter, Darmstadt (DE)

(73) Assignee: GSI Helmholtzzentrum fuer Schwerionenforschung GmbH, Darmstadt (DE)

( * ) Notice: Subject to any disclaimer, the term of this patent is extended or adjusted under 35 U.S.C. 154(b) by 123 days.

(21) Appl. No.: 13/513,583

(22) PCT Filed: Dec. 2, 2010

(86) PCT No.: PCT/EP2010/068716
§ 371 (c)(1),
(2), (4) Date: Jun. 4, 2012

(87) PCT Pub. No.: WO2011/067324
PCT Pub. Date: Jun. 9, 2011

(65) Prior Publication Data
US 2012/0241635 A1    Sep. 27, 2012

(30) Foreign Application Priority Data
Dec. 5, 2009 (DE) .................. 10 2009 058 294

(51) Int. Cl.
*G21K 5/00* (2006.01)
*A61N 5/10* (2006.01)

(52) U.S. Cl.
CPC ............ *A61N 5/1048* (2013.01); *A61N 5/1043* (2013.01); *A61N 5/1064* (2013.01); *A61N 5/1067* (2013.01); *A61N 2005/1087* (2013.01)

(58) Field of Classification Search
CPC .................................. A61N 5/10; G21K 5/00
USPC .......................................................... 250/389
See application file for complete search history.

(56) References Cited

U.S. PATENT DOCUMENTS

| 7,307,264 | B2 | 12/2007 | Brusasco et al. | |
|---|---|---|---|---|
| 7,590,219 | B2* | 9/2009 | Maurer et al. | 378/65 |
| 2005/0254622 | A1* | 11/2005 | Llacer | 378/65 |
| 2007/0140425 | A1 | 6/2007 | Kamikonya et al. | |

(Continued)

FOREIGN PATENT DOCUMENTS

| DE | 102007014715 A1 | 11/2008 |
|---|---|---|
| DE | 102007045879 A1 | 4/2009 |

(Continued)

OTHER PUBLICATIONS

European Patent Office, International Search Report in International Patent Application No. PCT/EP2010/068716 (Apr. 21, 2011).

*Primary Examiner* — Marcus Taningco
(74) *Attorney, Agent, or Firm* — Leydig, Voit & Mayer, Ltd.

(57) ABSTRACT

A method actuates a device for irradiating an object that has at least one target volume to be irradiated and at least one volume to be protected. The method includes defining at least one signal dose value for the volume to be protected and irradiating the object at least one of at least at times and at least in part with hadron irradiation. A dose introduced into the volume to be protected during the irradiation of the object is determined and at least one signal is emitted as soon as the introduced dose exceeds at least one signal dose value in at least one point of the volume to be protected.

20 Claims, 6 Drawing Sheets

(56) References Cited

U.S. PATENT DOCUMENTS

| | | |
|---|---|---|
| 2008/0002811 A1 | 1/2008 | Allison |
| 2008/0049896 A1 | 2/2008 | Kuduvalli |
| 2008/0292053 A1* | 11/2008 | Marash et al. .................. 378/65 |
| 2009/0010390 A1* | 1/2009 | Saoudi et al. .................. 378/97 |
| 2009/0147916 A1 | 6/2009 | Fallone et al. |
| 2009/0161827 A1 | 6/2009 | Gertner et al. |
| 2009/0175418 A1 | 7/2009 | Sakurai et al. |
| 2010/0108903 A1 | 5/2010 | Bert et al. |
| 2010/0301235 A1 | 12/2010 | Bert et al. |

FOREIGN PATENT DOCUMENTS

| | | |
|---|---|---|
| DE | 102009055902 A1 | 6/2011 |
| EP | 2116277 A1 | 11/2009 |

* cited by examiner

IRRADIATION METHOD AND DEVICE FOR CARRYING OUT THE METHOD

CROSS REFERENCE TO RELATED APPLICATIONS

This application is a U.S. National Phase application under 35 U.S.C. §371 of International Application No. PCT/EP2010/068716, filed on Dec. 2, 2010, and claims benefit to German Patent Application No. DE 10 2009 058 294.0, filed on Dec. 5, 2009. The International Application was published in German on Jun. 9, 2011, as WO 2011/067324A1 under PCT Article 21 (2).

FIELD

The present invention relates to a method for actuating a device for irradiating objects, whereby the object has at least one target volume to be irradiated as well as at least one volume to be protected. The invention also relates to a control unit for actuating an irradiation device for irradiating objects as well as to an irradiation device for irradiating objects.

BACKGROUND

Nowadays, objects are irradiated in many different realms of technology. A wide array of irradiation methods as well as a wide array of types of radiation are employed, depending on the concrete requirements of the application.

Thus, for instance, in some areas of technology, it is desirable to irradiate objects over the entire surface area and as uniformly as possible.

In other areas of technology, in contrast, specific parts of the object to be irradiated have to be irradiated with a specific, as a rule particularly high, dose while the other parts of the object are not irradiated at all or else only to a slight extent. An example of this is the structuring of microprocessors using electromagnetic radiation (in some cases, all the way into the X-ray range) as well as the structuring of imaging masks.

In yet other areas of technology, the dose distribution of the irradiation has to be structured not only in a two-dimensional plane but rather, in all three spatial dimensions. If applicable, a three-dimensionally structured irradiation with time variation has to be carried out (so-called four-dimensional structured irradiation). Such irradiation methods make it possible to introduce a specific, relatively high dose into a specific volume area located within an object that is to be irradiated. The area that surrounds the target volume that is to be irradiated, in contrast, can be exposed to a comparatively low dose. Examples of such a treatment of objects are found in the material sciences, in the manufacture of highly integrated components (especially microprocessors and memory chips) as well as in the production of nanostructured mechanisms.

Another field of technology that makes use of such three-dimensional or four-dimensional irradiation methods is that of medical technology. Here, it is likewise desirable to expose specific volume areas of the body, for instance, tumors, to the highest possible dose, whereas the surrounding tissue should only be exposed to the radiation dose to the smallest extent possible, or preferably not at all. This is particularly the case when the surrounding tissue is tissue such as, for example, one or more critical organs (usually referred to in technical terminology as OAR, short for "organ at risk"). Such a critical tissue can be, for instance, the spinal cord, major blood vessels (e.g. the aorta) or nerve nodes.

Such a desired selective irradiation "into the depths" of the object to irradiated can be achieved, for example, in that the irradiation takes place from many different directions, whereby all of the beams coming from different directions intersect at a specific point or in a specific target zone of the object to be irradiated. This translates into a high total dose at the point of intersection of the differently aimed beams, while the dose outside of this point of intersection is relatively low.

Another approach for achieving such a selective irradiation "into the depths" of an object consists of selecting certain types of radiation that, while passing through matter, display an energy-loss characteristic that has a peak that is as pronounced as possible. Examples of this are especially protons, ions and heavy ions. As they pass through matter, these types of radiation initially exhibit a relatively low energy loss per unit of length, so that the radiation dose deposited there is relatively low. On the contrary, most of the radiation energy is deposited in the so-called Bragg peak, so that the dose introduced into the object that is to be irradiated is very high there. As a result, a relatively sharply delineated target point can be reached "in the center" of an object that is to be irradiated. The dimensions of such a target point (or of a certain volume element, referred to in technical terminology as a "voxel") can be, for example, within the range of a mere 1 mm$^3$. A target volume to be irradiated having a specific contour can be selectively irradiated, for instance, by scanning methods, preferably by means of so-called raster scanning methods. Here, the target volume can be divided into so-called raster points. In this process, the particle beam (taking into consideration the Bragg peak) is passed successively over the target volume that is to be irradiated. A deflection in the X-Y plane (a so-called isoenergy plane) can be traversed by scanner magnets that can laterally deflect the particle beam. The depth can be varied by changing the energy of the particle beam, thus repositioning the Bragg peak. Whereas in the case of "classic" scanning methods, the particle beam is moved essentially continuously over the target volume, with the raster scanning method, the particle beam is always aimed at a raster point or voxel, where it remains for a certain period of time. As soon as a specific dose has been introduced into the voxel in question, the particle beam moves on to the next voxel.

Although the dose introduced into the object can be restricted relatively well to a certain volume area when heavy ions are employed, here as well, it is unavoidable that matter which is located in front of or behind the target point, especially along the particle beam, and which should actually not be irradiated, is exposed to a certain dose. This is particularly the case for regions that are in the front of the target area that is to be irradiated.

As a rule, the planning of the irradiation using currently available methods calls for the protection of organs at risk. The influence of movement that occurs during the irradiation, however, often cannot be adequately predicted. Consequently, when movement exerts an influence, the actual dose deposition in the target volume and/or especially in organs at risk can only be evaluated after the fact, if at all. Intervention is only possible with respect to fractions that might still follow. This, however, is problematic, particularly if the tumor is located in a critical tissue area (for instance, in an organ such as the lung or the heart), or if there is critical tissue in the immediate vicinity of the tumor. After all, with "normal" tissue, it is, in fact, possible to accept a certain, actually unnecessary, destruction of tissue, whereas in the case of such critical tissue (OAR), any damage should absolutely be avoided. In the past, this has often led to situations in which such tumors located near critical tissue could not be treated at all, or else at best only with severe side effects.

Especially problematic was the irradiation of target volumes in or near sensitive matter areas such as, for example, tumors in or near critical tissue, especially when the object in question moves, particularly when it moves of its own accord. Here, the matter surrounding the target volume to be irradiated can be moved not only translatorially, but also, and especially, rotatorially and/or deformatorially. As a consequence, for instance, if the beam position relative to the target volume or to the volume to be protected changes (due to the scanning method or also due to a change in the direction of the incident beam, for example, when a gantry is employed), the matter surrounding the target volume can be irradiated, for example, due to the movement "of its own accord" in the area of the incident particle beam; in particular, it might be irradiated differently than was intended in the preceding irradiation planning. This can cause a certain amount of damage to the affected tissue (the affected matter), which is particularly problematic if it is, for instance, a tissue that is to be specially protected (e.g. an OAR).

SUMMARY

In an embodiment, the present invention provides a method for actuating a device for irradiating an object that has at least one target volume to be irradiated and at least one volume to be protected. The method includes defining at least one signal dose value for the volume to be protected and irradiating the object at least one of at least at times and at least in part with hadron irradiation. A dose introduced into the volume to be protected during the irradiation of the object is determined and at least one signal is emitted when the introduced dose exceeds at least one signal dose value in at least one point of the volume to be protected.

BRIEF DESCRIPTION OF THE DRAWINGS

Exemplary embodiments of the present invention are described in more detail below with reference to the drawings, in which.

DETAILED DESCRIPTION

Figure 1:
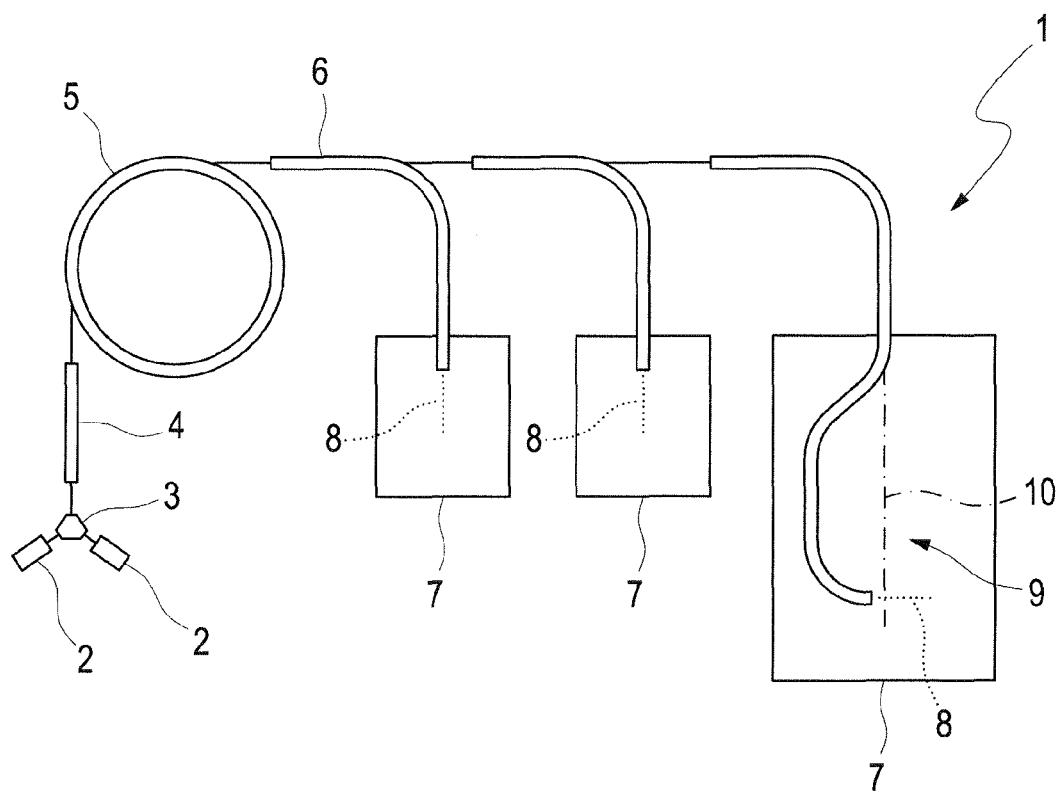
FIG. 1 shows a schematic depiction of an irradiation system.

In an embodiment, the present invention provides a method for actuating a device for irradiating objects, said method being an improvement over the current methods. Moreover, in an embodiment, an aspect of the invention is to provide a control unit that is improved in comparison to the state of the art and that serves to actuate an irradiation device for irradiating objects, and also to propose an irradiation device that is improved in comparison to the state of the art and that serves to irradiate objects.

In an embodiment, the present invention provides a method for actuating a device for irradiating objects, whereby the object has at least one target volume that is to be irradiated as well as at least one volume that is to be protected, whereby at least one signal dose value is defined for the volume to be protected and whereby, during the irradiation of the object, the dose introduced into the volume to be protected is determined, and at least one signal is emitted as soon as the introduced dose exceeds at least one signal dose value in at least one point of the volume to be protected. The volume to be protected can fundamentally be any volume areas of the object to be irradiated that lie outside of the target volume to be irradiated. Particularly so as to be able to ensure a sufficiently high dose inside of the target volume that is to be irradiated (especially at its edges), however, it is also possible that the term volume to be protected refers to a volume that is situated outside of a so-called safety margin, whereby the safety margin constitutes a layer that has a defined thickness and that is situated around the target volume to be irradiated. Furthermore, the volume to be protected can also be a volume area of the object that is highly sensitive to radiation and/or that, for other reasons (for instance, because highly critical elements are present in the volume area in question) has to be protected against radiation to the greatest extent possible.

Naturally, it is also possible that there are several (for example, two, three, four, five or more) target volumes to be irradiated and/or volumes to be protected which, if applicable, are separate from each other. In addition or as an alternative to this, it is likewise possible that, in the case of several volumes to be protected, two, a certain percentage, or else all of the volumes to be protected have different signal dose values. In this manner, the irradiation procedure also lends itself very well for complex structures. In particular, this ensures a very extensive protection of sensitive volume areas, for example, the protection of an OAR, while, at the same time, ensuring the best possible irradiation of the volume that is to be irradiated.

The type of irradiation can be a particle beam that preferably has a relatively small extension in one, two or more directions that run perpendicular to the direction of the beam. Especially preferably, this can be a needle-sharp beam. Although it is usually preferable for the particle beam to be a "homogenous" particle beam, especially a particle beam with one type of ions, for instance, carbon ions, it is also conceivable for the particle beam to consist of a mixture of two or more different types. Examples of particles are especially photons, leptons and/or hadrons. In particular, they can be pions, electrons, positrons, protons, ions and/or heavy ions. The term heavy ions normally refers to ions that have an atomic number $\geq 3$ and/or a mass number $\geq 5$. All of these beams can be emitted, at least at times and/or at least in part, at least quasi-continuously (in other words, they have an essentially uniform beam intensity at least for certain periods of time). By the same token, however, it is also possible for the irradiation to take place at least at times and/or at least in part while using at least one intensity-modulated beam. Incidentally, this refers not only to particle beams that have particles with a rest mass that does not equal zero, but also to beams that have photons. In this context, special mention should be made of the possibility of employing an intensity-modulated photon beam (which can be used, for instance, for so-called intensity-modulated radiation therapy—IMRT).

The object to be irradiated can fundamentally be any desired object such as, especially a workpiece that can consist, for instance, at least in part of a semiconductor material. By the same token, it is also possible for the workpiece to be a so-called "phantom" which is used in medical devices in order to simulate the effect of the technical device on a patient. Such phantoms are employed not only for the development of medical devices, especially for irradiation devices, but also especially in order to check or renew their calibration and/or to ensure the proper functioning of the device. For instance, such phantoms can be used daily at the beginning of the day of treatment so that, to the greatest extent possible, injury or even fatalities due to defective equipment can be ruled out. Phantoms can also be used to validate an irradiation plan. Of course, the object can also be an animal, a person or, in general, biological tissue. Particularly in the case of a person and/or an animal, the volume to be protected can be normal tissue and/or critical tissue (for example, the spinal cord) or an organ (especially a so-called organ at risk—OAR—such as, for instance, the lung or the heart). The target volume to be irradiated can especially be a tumor. With the method being proposed, the doses introduced into the volume (s) can especially be controlled continuously, in other words, especially also during the treatment, especially during the irradiation, preferably essentially during the entire treatment; in particular, these doses can be monitored and changed if necessary. Especially preferably, the dose introduced into the volume(s) to be protected can be monitored at least at times and/or at least in given areas, also in a spatially resolved manner. As a result, the method can ensure an especially high degree of safety. In particular, an appropriate suitable measure can be initiated at any point in time, such as a change in the irradiation parameters, for instance, the intensity of the particle beam, at least during the dose deposition in dedicated areas of the volume to be irradiated and/or of the volume to be protected, as soon as a signal dose value has been reached or is about to be reached. As a result, maximum protection of the patient can be attained, especially in terms of his/her critical tissues. After all, in the state of the art, the dose introduced into the volume to be protected is checked, if at all, after completion of the treatment step (in other words, for example, in the case of a scanning method, only after the volume to be protected has been scanned in its entirety). However, particularly when several unfavorable boundary conditions coincide, this point in time can be much too late, so that, for instance, a critical signal dose value might at times have already been exceeded by a large amount. Therefore, as a rule, the method being proposed entails a considerably higher level of safety in comparison to such prior-art methods.

With this method, it is especially possible to respond online during the treatment to changes in the dose deposition caused, for example, by movement. This means that it is possible to prevent the dose threshold values from being exceeded in the structures to be protected, especially in the volume to be protected.

The at least one signal dose value can especially be a warning dose value and/or a maximum dose that should not be exceeded. The warning dose value can especially be a value at which it is not absolutely necessary to take immediate drastic measures. Instead, as a rule, it is still possible to respond differently to such a warning dose value since a certain additional dose can still be introduced without this precipitating a critical situation. For example, when a warning dose value is reached, the next irradiation can be suitably changed. In contrast, the maximum dose that should not be exceeded can be a value that must not be exceeded in any case since this would otherwise have grave consequences such as, for instance, severe injuries. Naturally, it is also possible to provide a plurality of signal dose values, particularly also a plurality of warning dose values (whereby this can especially apply to one and the same volume area), so that on the basis of the associated risk potential, adapted measures can be taken in each case. It goes without saying that, especially if many different critical volumes are present, it is also possible to define different signal values or different sets of signal values. It should be pointed out here that the appertaining signal dose values do not necessarily have to be a fixed number (such as, for instance, 5 Gy or the like). Rather, the signal dose values can also be gleaned, for example, from a so-called dose-volume histogram (DVH). Such DVHs are based on the realization that, if a volume to be protected is going to be irradiated over its entire surface area, a lower limit dose is permissible than in a case when a volume to be protected is only exposed to radiation over a relatively small partial area (especially in a punctiform manner).

In particular, the method can be carried out in such a way that the emitted signal causes a termination of the irradiation procedure and/or an interruption of the irradiation procedure and/or a change in at least parts of the irradiation procedure that is still to be performed, especially a reduction of the dose that is to be introduced into at least parts of the target volume to be irradiated and/or into at least parts of the volume to be protected. The term interruption of the irradiation procedure especially refers to a certain time pause that can lie within a wide range, especially comprising seconds, minutes, hours, days, weeks or months. This time can be employed, for example, in tumor therapy, to allow the patient to recuperate in the meantime, or else to readjust the device being used for the irradiation. For instance, this interval can be utilized to draw up a new irradiation plan or to appropriately adapt it, to reposition the patient and/or to adjust a gantry. By the same token, it is also possible for the method to be carried out continuously and for the irradiation plan to be recalculated and/or adapted, for instance, online during the ongoing irradiation, or else for the patient to be repositioned with respect to the particle beam during the ongoing irradiation (e.g. by rearranging the patient and/or by moving a gantry). A termination of the irradiation procedure can be advisable, especially in those cases when the value has reached or has even exceeded the maximum dose that should not be exceeded. "Gentler" countermeasures (such as, for instance, changing at least parts of the irradiation procedure that is still going to be carried out and/or interrupting and later resuming the irradiation procedure) are especially recommended when only a warning dose value was reached or exceeded. Of course, aside from a change in the irradiation plan or in the direction of the incident beam, it is also possible to initiate other measures such as, for example, so-called "gating", a periodical switching on and off the particle beam and/or so-called "re-scanning" with changed irradiation parameters.

It is advantageous for the introduced dose to be at least at times or at least in part the administered dose and/or the deposited dose. The administered dose is normally determined in that the actually performed radiation is measured (in the case of a particle beam, for example, by measuring the beam, especially by measuring the beam position and/or the beam intensity and/or the beam energy), and the administered dose is calculated by at least partially using these measured values. Consequently, as a rule, the determination of the applied dose involves measured values, whereby, however, the introduced dose is normally not determined directly in the object that is to be irradiated but rather, only indirectly. With the deposited dose, in contrast, the introduced dose is determined directly in the object that is to be irradiated, especially in the target volume and/or in the volume that is to be protected, for which purpose implanted detectors, for example, can be used, or else external detectors (in other words, detectors that are not implanted) such as, for instance, a so-called PET (PET stands for photon emission tomograph). Of course, however, it is also possible that, at least at times and/or at least in part, the introduced dose is determined on the basis of the control data of the irradiation device or the like, for instance, with the aid of a measurement of the movement of the target volume in the case of moved objects, especially a moved target volume, and/or a volume that has to be protected.

Especially advantageously, the method can be carried out when the dose introduced into the volume to be protected and/or the dose introduced into the target volume to be irradiated is determined at least in part and/or at least at times using at least one measured value that has been measured in the volume in question and/or in the beam, whereby the measured value determined in the beam is especially the beam position, the beam size, the beam shape, the beam intensity and/or the beam energy. Thanks to such a use (at least in part) of current measured values, the precision of the method can be further enhanced. The beam intensity can especially be the so-called integrated beam intensity. When the measured value is determined in the volume in question, an implanted measuring device and/or measuring device that is not implanted (such as, for example, a photon emission tomograph—PET) can be employed in any desired manner.

It is likewise advantageous to use the method when the object to be irradiated moves at least at times and/or at least in given areas, especially at least at times and/or at least in given areas, of its own accord, whereby especially the target volume to be irradiated and/or the volume to be protected moves at least at times and/or at least in given areas, particularly they move at least at times and/or at least in given areas, relative to each other. The term movement here refers not only to a translatory movement, but especially also to a rotatory movement and/or to an expanding movement of the appertaining volume area(s) and/or of the volume areas that might lie in-between. Such moving volumes make very high requirements of the irradiation method or irradiation device, whereby, thanks to the proposed method, it is possible to attain a very high level of protection for the object to be irradiated (for instance, the patient, if applicable, including tissue areas that are to be especially protected, particularly including the patient's OARs). In the case of the irradiation of a tumor of a patient, such cases might occur, for instance, if the tumor is located in the area of the lung, of the heart and/or of the intestine (or in the vicinity thereof). If, purely for the sake of an example, a tumor (or another so-called clinical target volume—CTV) located in the lung is under observation, it not only moves but it is also situated near the spinal cord as well as in the vicinity of the moving mediastinum and possibly also in the vicinity of the beating heart, whereby the spinal cord, the mediastinum and the heart are all highly critical tissues or organs that therefore have to be treated with utmost care.

It is likewise possible to carry out the method in such a way that, at least at times and/or at least in given areas, the position of at least parts of the object to be irradiated is measured, especially, at least in part or at least at times, employing an imaging method. In particular, the parts of the object to be measured can be at least the one target volume to be irradiated and/or the at least one volume to be protected. Once the position of at least parts of the object to be irradiated is known, on the one hand, the irradiation can be adjusted more precisely (particularly at the beginning of the irradiation procedure) and, moreover, if applicable, movement of the target volume to be irradiated and/or of the volume to be protected that occurs during the irradiation can be recorded and taken into consideration, if applicable. An essentially continuous monitoring of the position (and thus of the movement) of at least parts of the object to be irradiated (referred to in technical terminology as "motion tracking" or "tumor tracking") is particularly advantageous for so-called "motion mitigation" methods, here especially to the method known in technical circles as "beam tracking". Optionally, the tracking method can also be another method such as, for instance, the so-called "gating" method. Combinations of the above-mentioned methods as well as optionally other methods such as, for instance, gating or re-scanning are likewise conceivable.

Particularly when measurements of the movement are carried out, it is recommended for the measured values and/or the results obtained from the measured values to be taken into account for the current irradiation and/or for the subsequent (partial) irradiation procedures. This can be done, for example, by changing the beam guidance, changing the scanning, adapting the irradiation plan or the like. As a result, the irradiation quality can be enhanced, at times even considerably.

It is also particularly advantageous if the method is carried out in such a way that the irradiation takes place in the form of a scanning procedure, especially a raster scanning procedure. A scanning procedure normally takes place in such a way that the place where the main dose is introduced is essentially continuously changed, at least at times. Certain interruptions are possible here, for instance, when a change is made from one "irradiation line" to the next one and/or when the isoenergy plane is changed. With the raster scanning procedure, in contrast, the beam is normally moved "abruptly" from one irradiation point to the next irradiation point. The beam normally remains for a certain time at each irradiation point, until a certain (partial) irradiation dose is reached in the point in question. In particular, it is also possible for the scanning procedure and/or the raster scanning procedure to take place at least at times and/or at least in given areas in an intensity-modulated manner. Merely for the sake of completeness, it should be pointed out that it is also possible to conduct the scanning procedure and/or the raster scanning procedure only at times and/or only in given areas.

Another advantageous refinement of the method can be achieved if the irradiation takes place in the form of several partial irradiation procedures, especially in the form of several fractions and/or several re-scanning procedures and/or by employing gating methods. The term gating method normally refers to the fact that the particle beam is switched on and off in a modulated manner as a function of a movement of the object and/or of the target volume that has been measured and/or that was known prior to the irradiation. The switching on and off can be done, for instance, when a tumor (or another volume area that is to be irradiated) moves briefly outside of the area that can be reached by adjusting the beam. In particular, however, gating refers to a technique that reduces the influence that the movement has on the irradiation since the irradiation beam is only switched on during certain states of motion of the tumor (e.g. at the end of exhalation).

Occurring local fluctuations that can lead to the beam being temporarily switched off can be relatively rare, especially when gating methods are combined with tracking methods. When it comes to so-called re-scanning procedures, the total dose that is to be introduced is normally divided into several partial procedures, so that movements of the tumor (of the volume to be irradiated) average out within the statistical mean. The term factions normally refers to the division of a treatment (irradiation) into several partial irradiation procedures that are staggered over time with respect to each other. The time interval between two partial irradiation procedures in fractionated irradiation is normally in the range of hours to days although it can also be weeks and/or months. Such a division into several partial irradiation procedures often renders the method more effective, especially in medical applications, and can also often be carried out in a manner that is less stressful to patients.

Furthermore, a control unit is proposed for actuating an irradiation device for irradiating objects, which is configured and set up in such a way that it carries out the method described above, at least at times. The control unit then analogously has the above-mentioned advantages and properties. In particular, it is possible to refine the control unit as set forth in the description above (if applicable, with suitable adaptations). The control unit can be any device whose functionalities are implemented through hardware in any desired manner, and/or it can be a device whose functionalities are implemented through software. Mixed forms are also conceivable, namely, in such a way that some functionalities are implemented by hardware while others are implemented by software. In the case of implementation through software, the control unit can comprise one or more computers or computer components. Here, this can especially refer to personal computers (CPs), mainframes, workstations or even single-board computers. It is likewise possible for the computing load to be distributed among a plurality of different computers or computer components.

Moreover, an irradiation device for irradiating objects is being proposed that has at least one control unit with the structure described above. Then, the irradiation device also entails the above-mentioned properties and advantages in an analogous manner. Furthermore, the irradiation device can be refined as set forth in the description above.

In particular, it is possible for the irradiation device to have at least one measuring device, especially at least one beam measuring device and/or at least one movement measuring device, whereby the beam measuring device can especially be configured as a beam position measuring device, a beam intensity measuring device and/or a beam energy measuring device. In particular, the beam measuring devices can be configured, at least in certain areas, as ionization-chamber devices and/or as multi-wire chambers. Such components normally increase the irradiation precision of the irradiation device when it is used to irradiate an object. Precisely the proposed components normally exert a very high influence on the improvement of the precision of the irradiation. Ionization chamber devices as well as multi-wire chambers have also proven their worth for the measuring tasks for which they are responsible, and they are readily available (also commercially).

The acceleration device can especially be a particle accelerator that can have, for example, at least one linear accelerator, at least one synchrotron and/or at least one cyclotron. Combinations of the above-mentioned (as well as other) acceleration devices are likewise conceivable. For instance, synchrotrons normally have a linear accelerator as a pre-accelerator. The acceleration device can supply a particle beam that has the beam parameters needed for the irradiation of the target volume. However, the accelerator device can also be an accelerator with a laser device to generate the beam or it can be an accelerator referred to as a "dielectric wall" (DWA). The method according to the invention and the irradiation device according to the invention, however, are largely independent of the method by means of which the therapy beam is provided.

FIG. 1 is a schematic overview showing the set-up of an embodiment of an irradiation system 1 that uses a particle beam 8 to irradiate a partial area of a body 34 such as, for example, diseased tissue 14 with a tumor in the body 34 of a patient. The particles employed can especially be ions (usually cations) such as, for instance, protons, pions, helium ions, carbon ions, neon ions, etc. as well as mixtures of two or more of the above-mentioned particles as well as other particles, if applicable.

Normally, such particles are generated in a particle source 2. In the embodiment of the irradiation system 1 shown in FIG. 1 and designated as the irradiation device 1, two particle sources 2, for example, two ECR ion sources are provided, so that two different types of particles can be generated. This makes it possible to switch over between these two particle types within a short time. If applicable, it is also possible to simultaneously generate a mixture of both particle types by operating both particle sources 2 at the same time. In order to be able to switch over between two different particle types, a switching magnet 3 is provided that is arranged between the particle sources 2 on the one hand, and a pre-accelerator 4 on the other hand. The switching magnet 3 can also be operated in a mode in which the particles generated by the two particle sources 2 are simultaneously conveyed to the pre-accelerator 4, so that a particle mixture is created.

The particles generated by one or both of the particle sources 2 and, if applicable, selected with the switching magnet 3 are accelerated to a first energy level in the pre-accelerator 4. The pre-accelerator 4 is configured, for example, as a linear accelerator (LINAC). After the pre-acceleration, the particles are fed into an accelerator ring 5 that is configured, for instance, as a synchrotron or cyclotron. In the accelerator 5, the particles are accelerated from the initial, first, comparatively low energy level to high energies of the kind needed for the irradiation. After the particles have left the accelerator ring 5, a high-energy beam transportation system 6 conveys the particle beam 8 to one or more irradiation spaces 7.

In an irradiation space 7, the accelerated particles are aimed at the object 34 to be irradiated, especially a body 34. This can be, for instance, a patient who is lying on a table. Depending on the configuration, the particle beam 8 is applied onto the body 34 from a fixed direction (in so-called "fixed beam" spaces), or else from different directions, for which purpose a gantry 9 that can be rotated around an axis 10 is provided. In the embodiment of the irradiation system 1 shown here, only a single gantry 9 is provided for a total of three irradiation spaces 7, since experience has shown that a rotatable gantry 9 is not absolutely necessary for most of the treatments that are to be carried out. Since a rotatable gantry 9 entails significant costs, considerable savings can be achieved in this manner. Of course, it is likewise possible that none, most, or all of the irradiation spaces 7 are provided with a gantry 9.

Moreover, FIG. 1 indicates the particle beam 8 that is released in the irradiation spaces 7.

Figure 2:
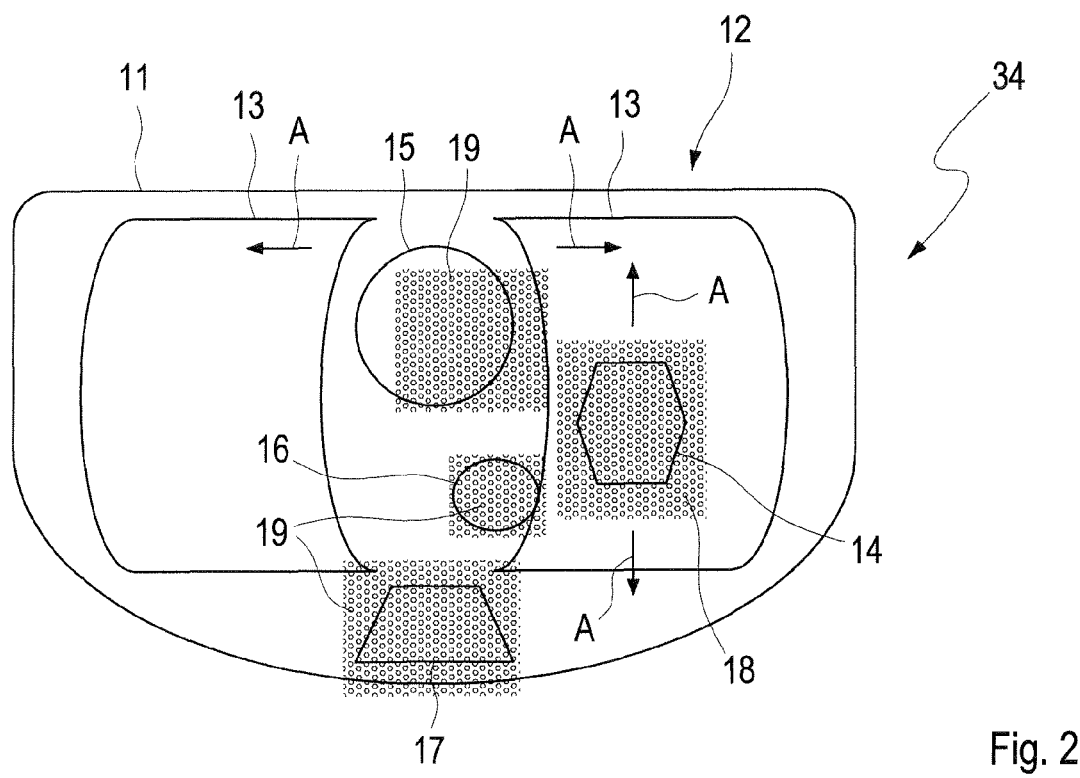
FIG. 2 shows a schematic depiction of a tumor that is to be irradiated and that is located in the area of the lung of a patient, including critical tissue areas situated in the vicinity.

As an example of a body 34 to be irradiated, FIG. 2 shows a cross section through the chest 11 of a patient at the height of the lung 12. FIG. 2 depicts both lung lobes 13, whereby one of the two lung lobes 13 is diseased with a tumor 14. This tumor 14 constitutes the target volume 20 that is to be irradiated by the irradiation system 1. When it comes to irradiation by the irradiation system 1, the objective is to damage or destroy the region of the tumor 14 by exposing it to a sufficiently high dose, especially a particle dose, preferably an ion dose.

Furthermore, FIG. 2 shows three critical structures 15, 16, 17 (risk structures, also referred to as organs at risk—OARs—in technical terminology). To be precise, these are the spinal column 17 with the spinal cord located therein, as well as the aorta 16 and the mediastinum 15.

Owing to the patient's breathing during course of the treatment, certain parts of the chest 11 move. This is indicated in FIG. 2 by several arrows A. In particular, the tumor 14 as well as the mediastinum 15 move significantly. This does not necessarily mean that the spinal column 17 and/or the aorta 16 do not move or cannot move. Normally, however, their motion is considerably less than is the case with the mediastinum 15 or with a tumor 14 located on a lung lobe 13.

Especially in the area of soft tissues, the movement of the tissue structures is not limited only to a translatory movement. On the contrary, as a rule, there are also rotatory movements (rotations) and/or extending movements (extension or compression of tissue structures). Such movements additionally complicate the problem, especially when these movements overlap, at least partially.

FIG. 2 also shows the rasters 18, 19 associated with the appertaining body parts 14, 15, 16, 17. In the case of the tumor 14, this is a target raster 18, which is reached by a particle beam 18 within the scope of the raster scanning therapy. In the case of the tissue structures 15, 16, 17 that are to be protected, in contrast, this is a register raster 19 with which the radiation (which is actually undesired or to be avoided) of the appertaining tissue structures 15, 16, 17 is registered.

Figure 3:
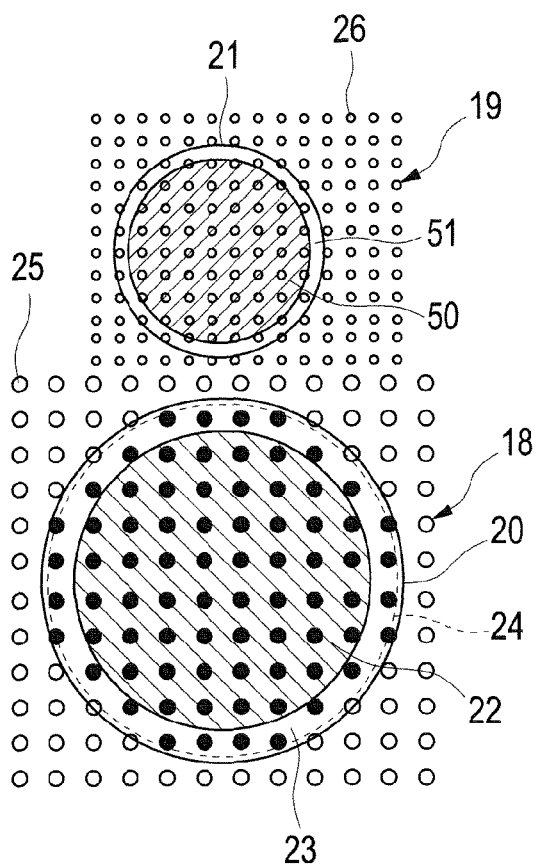
FIG. 3 shows a schematic depiction of target points of a target volume and of register points of a volume that is to be protected.
Figure 4:
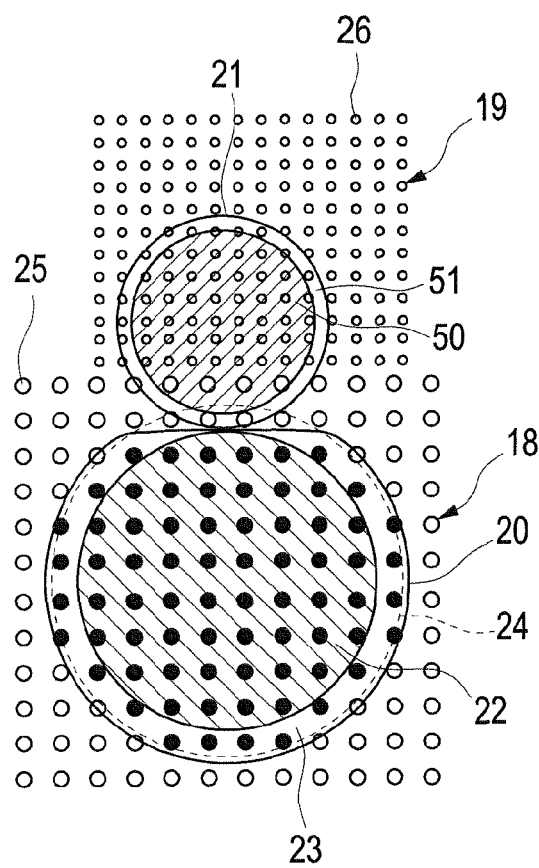
FIG. 4 shows a schematic depiction of target points of a target volume and of register points of a volume that is to be protected, in a second position.

FIGS. 3 and 4 show the situation depicted in FIG. 2 once again in a schematically simplified manner. In this context, for the sake of simplicity, FIGS. 3 and 4 only show a single target volume 20 to be irradiated as well as a single critical tissue 21 that is to be (particularly) protected. The inner area 22 of the target volume is depicted in FIGS. 3 and 4 by means of a sectional area that is hatched from the upper left to the lower right. The inner area 22 is, for example, the actual tumor area 14, in other words, the tissue that is actually diseased. In order to be able to completely destroy the tumor with a high level of certainty, it is a normal procedure to provide a so-called safety margin 23, which is also exposed to a high radiation dose, around the actual inner area 22. In addition, FIGS. 3 and 4 show a so-called isodose 24 drawn in the form of a broken line. Here, areas located within the isodoses 24 are exposed to a dose corresponding to ≥95% of the maximum dose.

Furthermore, FIGS. 3 and 4 also show critical tissue areas 21. Analogously to the target volume 20, also in the case of the critical tissue areas 21, there is also an inner area 50 that encompasses the organ tissue that is actually to be protected. For safety reasons, the inner area 50 is likewise surrounded by a safety margin 51. Therefore, the inner area 50 and the safety margin 51 form the volume of the critical tissue area 21. In the area of the target volume 20 as well as in the area of the critical tissue area 21, there is a raster 18, 19 that is configured as an array of finite volume elements 25, 26. The corresponding rasters 18, 19 extend three-dimensionally as a rule. The individual volume elements 25, 26 can be arranged here essentially in any desired manner, for instance, in cuboidal, rectangular, hexagonal or other rasters.

In the area of the target volume 20, there is a target raster 18 that normally consists of a large number of target points 25. Each of the target points or raster points 25 can be reached by the particle beam 8. Towards this end, the particle beam 8 can be moved laterally (within a so-called isoenergy plane 49) by scanner magnets 35, 36. In order to be able to reach different isoenergy planes 49, the energy of the particle beam 8 that has been applied to the body 34 to be irradiated can be varied by means of suitable devices 37. For the target point 25 in question, a particle number, and thus a corresponding associated dose, is defined by the number of particles that flow within a unit of time and by the length of the time interval within which the particle beam 8 is aimed at the target point 25. The blank circles in FIGS. 3 and 4 depict target points 25 at which the particle beam 8 is not aimed, or else which are exposed only to a small number of particles. Solid circles depict target points 25 which are exposed to a large number of particles.

A register raster 19 is provided in the area of the critical tissue area 21. The finite volume elements 26 which make up the register raster 19 are normally referred to in technical terminology as voxels 26. In contrast to the target points 25, the voxels 26 generally cannot be reached by the particle beam 8. However, when the particle beam 8 nevertheless passes through the critical tissue area 21 on its way to the target volume 20, a dose, albeit a relatively small one, is inevitably deposited into the appertaining tissue areas. This dose load is registered in association with a single voxel 26.

In FIGS. 3 and 4, the target volume 20 and the critical tissue area 21 are at a different distance from each other. Such a change in the distance can be brought about, for instance, by the breathing movement of the patient. If the target volume 20 and the critical tissue area 21 are directly adjacent to each other, as is shown in FIG. 4, then the irradiation that is deposited by the particle beam 8 can very easily lead to a disproportionately high and undesired (conceivably even critical or dangerous) irradiation deposition in the target volume 21. According to the method being proposed, however, the irradiation input that is provided by the particle beam 8 in the greater surroundings of the critical tissue area 21 is registered for every single voxel 26 in the register raster 19. By means of a summing-up operation, the total dose input per voxel 26 can be determined. In the example shown in FIG. 4, the irradiation input in the transition area between the critical tissue area 21 and the target volume 20 was so high that a signal value (warning dose) was exceeded for individual voxels 26. As a result, the irradiation intensity of individual target points 25 in the target raster 18 was reduced (which can be seen from the fact that the individual target points 25 are now depicted as blank circles and no longer as solid circles). Effectively, this results in the fact that, in the embodiment shown in FIG. 4, the safety margin 23 of the target volume 20 to be irradiated was markedly reduced in the area adjacent to the critical tissue area 21.

However, if the critical tissue area 21 and the target volume 20 move further apart because of the breathing of the patient, the affected target points 25 can once again be included in the scanning procedure at the high dose, resulting once again in the situation depicted in FIG. 3.

Figure 5:
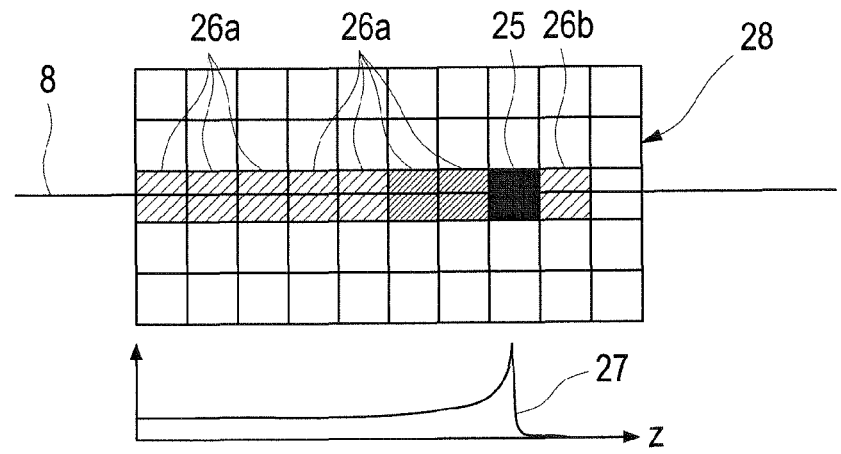
FIG. 5 shows a schematic depiction of the different dose inputs of a needle-sharp ion beam under the influence of movement.
Figure 5:
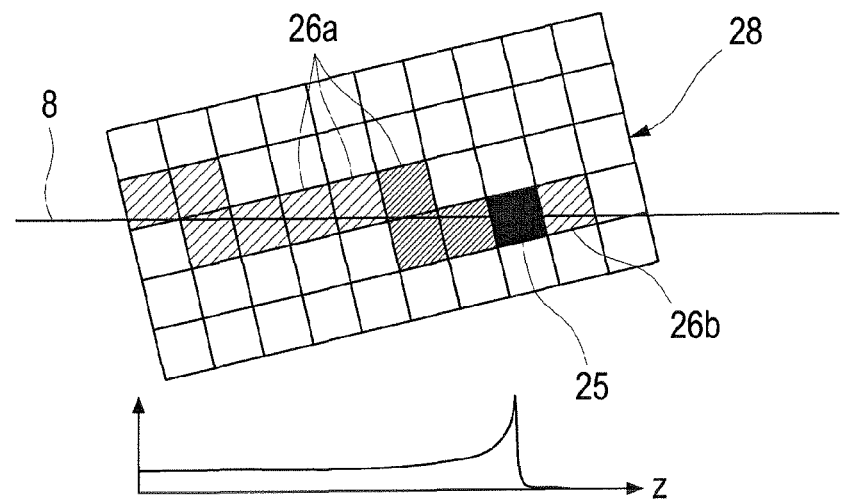
Figure 5:
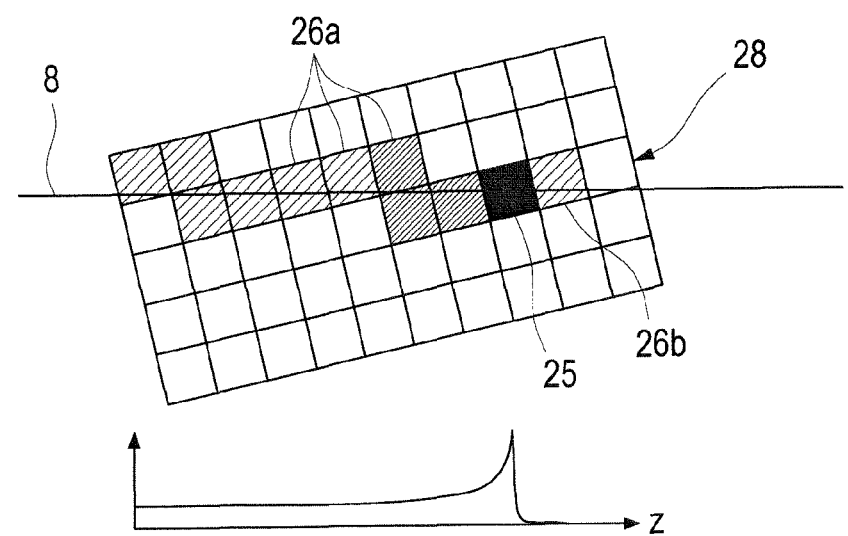

FIG. 5 illustrates how the voxels located in front of the target point 25 are exposed to a certain dose by the incident particle beam 8. Although the majority of the irradiation energy in a heavy-ion particle beam 8 is emitted in the so-called Bragg peak 27, so that most of the dose exposure is indeed released in the target point 25 (or in the target volume 21), a certain dose is nevertheless introduced into the voxels 26a located in front of the target point 25 as well as into the voxels 26b located behind the target point 25 (in FIG. 5, only a single voxel 26b has been drawn behind the target point 25). As can be seen in FIG. 5, the dose input into voxels 26a located in front of the target point 25 is normally higher than into voxels 26b located behind the target point 25.

FIGS. 5b and 5c show how a not only translatory movement of the tissue section 28 can cause different voxels 26 that have, in fact, not been reached by the particle beam 8 to receive a dose input (in particular, see the comparison between FIG. 5b and FIG. 5c). In this context, FIG. 5b depicts the situation without adaptation of the beam position to the movement (beam tracking), whereas FIG. 5c depicts the situation with beam tracking. This can be seen from the fact that in FIG. 5c, the Bragg peak is once again in the same voxel as in FIG. 5a. FIG. 5 particularly shows how a rotation of the tissue section 28 can cause completely different voxels 26, which are not actually exposed to the particle beam 8, to receive a dose input. In particular, it becomes clear that the dose load of the voxels 26 can change, even when beam tracking is being used. With this method, the dose input for each individual voxel 26 located outside of the target point 25 (or of the target volume 21) is continuously registered online, and preferably also the cumulative total dose that is introduced in each case. When certain values (such as, for instance, warning dose values and/or alarm dose values) are exceeded, appropriate measures are taken such as, for example, the "switching off" of individual target points 25 (see FIG. 4, especially in comparison to FIG. 3).

In FIG. 5b, due to a movement (for instance, breathing movement) of the target volume 20 or of the target point 25, the particle beam 8 briefly migrates away from the "actually" planned target point 25. For this reason, there is a (brief) beam deviation of one voxel length in FIG. 5b. Accordingly, it is the case that different voxels 26 and target points 25 are also irradiated. In FIG. 5c, the tracking method is once again active, and now the "actually" planned target point 25 is once again irradiated.

In the situation depicted in FIG. 5b as well as in the one shown in FIG. 5c (of course, also in the situation depicted in FIG. 5a), the dose magnitude for all of the voxels 28 or target points 25 that have actually been irradiated (to different degrees) is detected. The "faulty irradiation" according to FIG. 5b can be taken into account and preferably compensated for by means of an appropriately corrected beam guidance/irradiation plan in the next scanning procedure(s) with the particle beam 8. In particular, the requisite compensation of the "faulty irradiation" can be done online and in the same and/or in one or more subsequent irradiation procedure(s).

Figure 6:
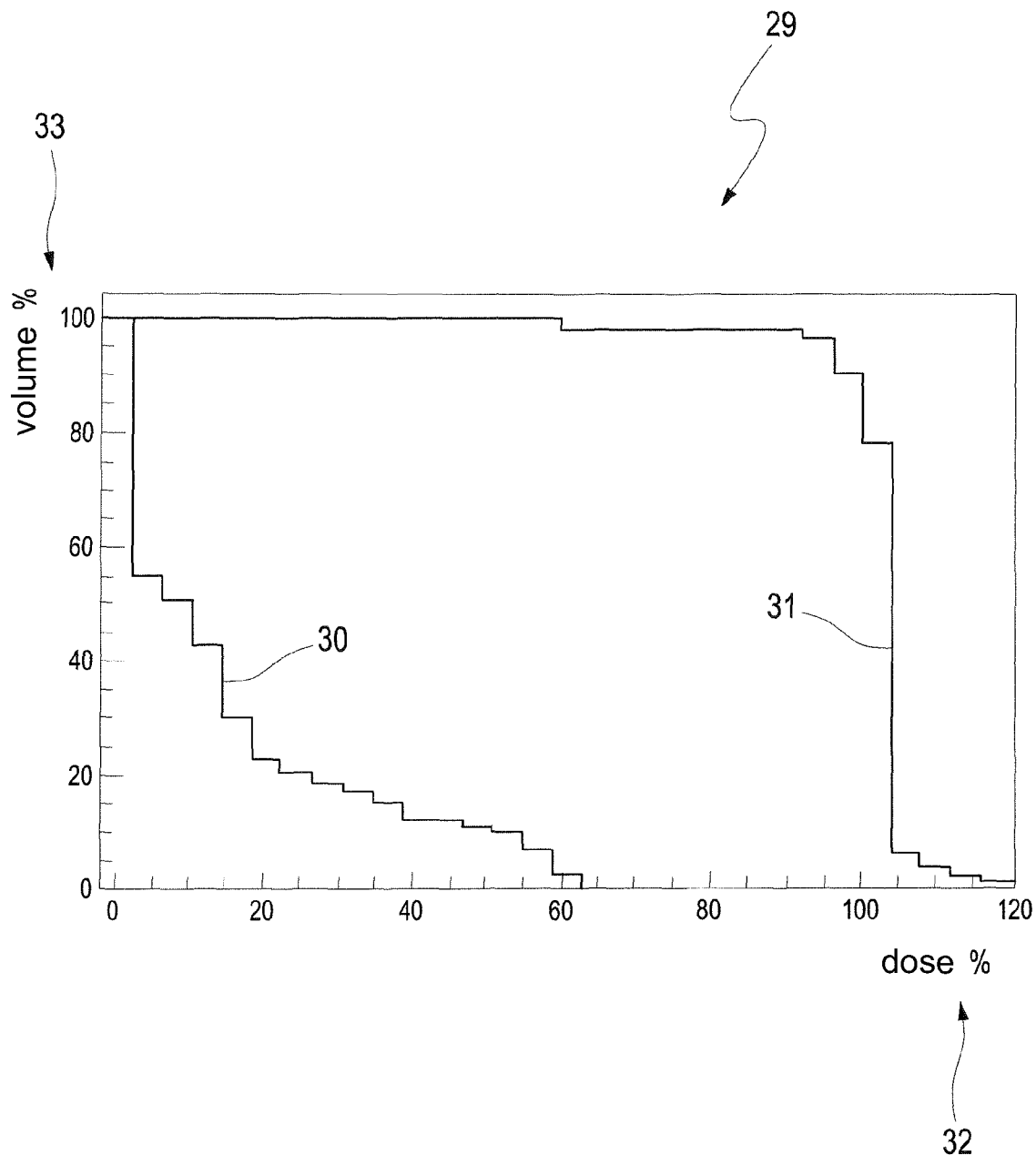
FIG. 6 shows an example of a dose-volume histogram.

FIG. 6 shows that the signal values (especially the warning values 30 and/or the maximum values 31) do not necessarily have to be present in the form of a fixed numerical value. Instead, it is also possible (and incidentally also preferred) for the magnitude of the dose values 30, 31 that bring about the emission of a signal to change as a function of the size of the irradiated volume (such as, for example, the irradiated volume of a critical organ). Such reciprocal relationships are familiar in the form of so-called dose-volume histograms (DVH) 29. A typical example is shown in FIG. 6. Here, the dose is plotted in % along the abscissa 32, while the relative irradiated volume fraction and/or the volume fraction to be irradiated is plotted along the ordinate 33. The curve 31 here designates, for instance, the DVH for the target volume that is to be irradiated. The curve 30 designates the maximum dose that the volume to be protected may receive. Therefore, the curve 30 constitutes a maximum value for the volume to be protected. Then the warning value can be determined from the maximum value. As can be seen in the DVH, higher dose values are permissible if they are limited to a relatively small volume region. However, if the region in question is irradiated over its entire surface, especially if it is essentially completely irradiated, then the permissible values for triggering a warning signal (warning value) as well as for triggering a maximum signal (maximum value) are in part considerably lower. For example, it is also common practice to define maximum values for parts of the organs at risk, A "V20" maximum value of 40 Gy, for instance, stipulates that the 20% of the affected organ at risk at the highest dose load must not exceed 40 Gy, at least not completely. The warning value can especially be between 50% and 90% of the maximum value.

Figure 7:
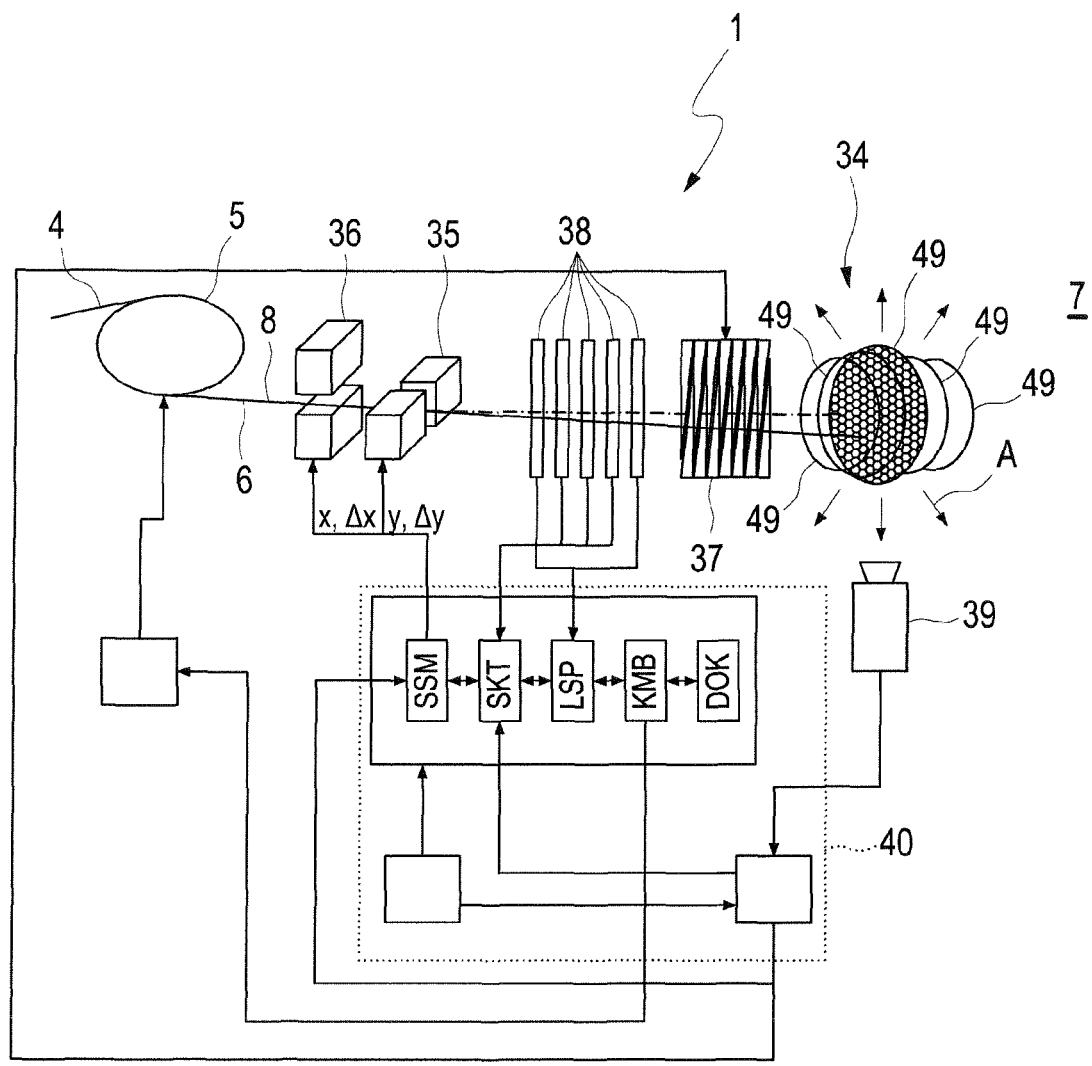
FIG. 7 shows a schematic depiction of an embodiment of an irradiation device with control elements.

FIG. 7 schematically depicts the already presented irradiation system 1 one more time. Although FIGS. 1 and 7 show the same irradiation system 1, each schematic drawing focuses on different components of the irradiation system 1. The particle beam 8 generated by the irradiation system 1 and extracted from the accelerator ring 5 is conveyed via the high-energy beam transportation system 6 to the body 34 that is to be irradiated and that is located in the irradiation space 7. The body 34 that is to be irradiated here comprises the irradiated body regions 14 (shown in greater detail in FIG. 2) or the body regions that are not to be irradiated (including the particularly sensitive tissue structures 15, 16, 17). As is indicated by arrows A, the body 34 moves, in particular of its own accord (shifting, rotation, extension and compression of the individual tissue regions 28 of their own accord and with respect to each other).

In order to reach all of the target points 25 of the target raster 18—which lies in the area of the target volume 20 that is to be irradiated (see FIGS. 3, 4)—first of all, a vertical scanner magnet 36 as well as a horizontal scanner magnet 35 are provided. They can be used to laterally move the site of action of the particle beam 8 (in other words, in the X and Y directions if Z stands for the direction of the particle beam 8) within an isoenergy plane 49 of the body 34 to be irradiated. The site of action of the particle beam 8 is varied in the Z direction by means of a particle-beam energy adaptation device 37 that is configured here as an energy absorber 37. The energy absorber 37 shown in FIG. 7 consists of a plurality of wedge-shaped elements made of an energy-absorbing material. The wedges located at the top and bottom of FIG. 7 are joined to each other to form a wedge block. Servomotors (not shown here) can move the two wedge blocks of the energy absorber 37 towards each other as well as away from each other. Depending on the position of the two wedge blocks relative to each other, the particle beam 8 has to traverse a path of different length through the energy-absorbing material of which the wedges of the wedge block are made. The beam loses a corresponding amount of energy as it passes through the energy absorber 37, so that the energy of the particle beam 8 that strikes the body 34 can be quickly changed (within certain limits) by means of the energy absorber 37.

Between the scanner magnets 35 and 36 as well as the energy absorber 37, there are also different detectors 38, some of which are configured here in part as gas-filled multi-wire chambers, and conversely, some of which are configured as so-called ionization chambers. The position of the particle beam 8 as well as its energy (before it passes through the energy absorber 37) can be determined with the detectors 38. In conjunction with the actuating signal of the energy absorber 37 (whereby the position of the wedge blocks can be determined, for instance, by means of suitable measuring devices), it is also possible to determine the energy of the particle beam 8 that strikes the body 34.

It goes without saying that the scanner magnets 35, 36, the absorber 37 and the detectors 38 can also be arranged in a different sequence. Already with the above-mentioned control signals and measured values, the control unit 40 is capable of determining the dose (especially the applied dose) that is introduced into the various voxels 26 in the body 34. This refers not only to the dose that is introduced into the target volumes 21 to be irradiated, but also and especially to the dose that is introduced (which in fact is not desired) into critical tissue areas 21 and/or into other tissue areas. The appertaining information is available here in a spatially resolved manner since the introduced dose is registered per voxel 26. By summing up the individual dose amounts, the dose that is accumulated per voxel 26 over the course of the irradiation procedure in all of the different tissue areas at every point in time can be read out essentially without delay. For this purpose, the method to be employed can especially be the one cited in the patent application bearing the title "Method and device for controlling the dose administration during irradiation" and filed by this applicant under the applicant's reference no. P 286 as a patent application at the German Patent and Trademark Office under the official application number DE 10 2009 055 902.7 on Nov. 26, 2009. The content of German patent application DE 10 2009 055 902.7 is hereby included in its entirety in the disclosure content of the present application.

If the accumulated introduced dose exceeds a certain limit value (warning value/maximum value), then a signal to this effect is emitted by the control unit 40. The signal value here can be dependent on the magnitude of the irradiated volume (see FIG. 6).

In order to further improve the precision of the irradiation, a PET 39 (PET stands for photon emission tomograph) is additionally provided for the irradiation system 1 shown here. The PET especially makes it possible to measure the dose that has been deposited in the body 34. If the PET 39 is capable of measuring in a spatially resolved and/or time-resolved manner, the corresponding measured values can also be used in a spatially resolved (directly) and/or time-resolved manner. Even if the PET 39 cannot measure in a spatially resolved manner, a spatially resolved measurement is nevertheless possible in an indirect way (with limited precision) by using the other measuring and control signals.

Instead of or in addition to a direct dose measurement, it is possible to measure especially the movement of the object and/or the target volume contained therein and/or the volume to be protected. On this basis, preferably in conjunction with a four-dimensional irradiation plan (4D-irradiation plan), the introduced dose can be determined online during the irradiation.

As already mentioned, the control unit 40 responds differently, depending on whether a signal—and if applicable which—signal is being generated or emitted. If a maximum signal is being generated or emitted, then the control unit 40 can effectuate, for example, a fast switching off of the particle beam 8. If, in contrast, only a warning dose value has been reached or exceeded, the control unit 40 can suitably adapt the subsequent parts of the raster scanning method. This can be done, for instance, by gating, by re-scanning and/or by modifying the irradiation plan. Since a complete recalculation of an irradiation plan is generally quite time-consuming (typically in the range of several hours), it is possible to simply modify the irradiation plan. In this context, especially the above-mentioned method of DE 10 2009 055 902.7 is employed.

Figure 8:
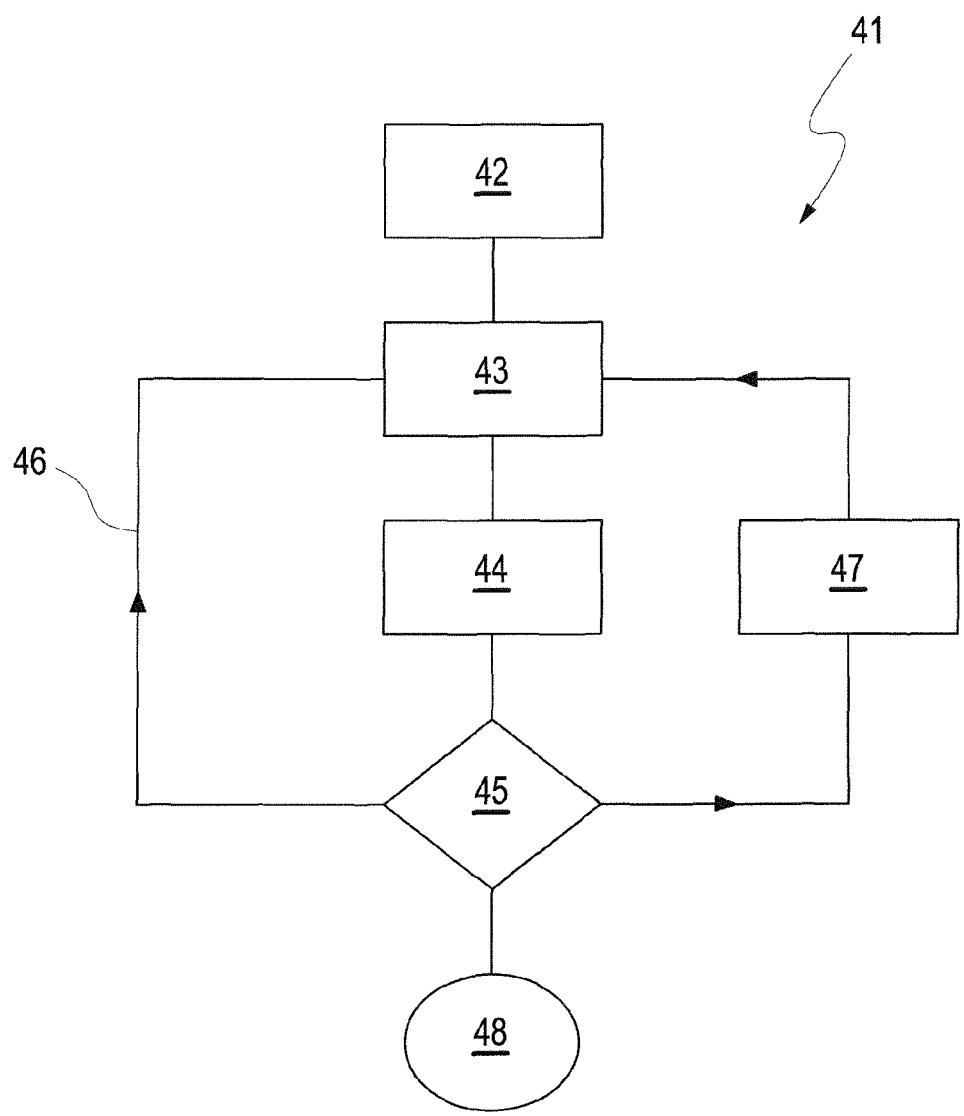
FIG. 8 shows a schematic depiction of a sequence of an irradiation method.

Finally, FIG. 8 schematically shows another conceivable flow diagram of the proposed irradiation method 41. In the irradiation method 41, first of all, a setpoint irradiation 42 is assumed. This setpoint irradiation 42 can be present, for example, in the form of a generally familiar irradiation plan. On the basis of the values of the setpoint irradiation 42, the individual components of the irradiation system 1 are appropriately actuated 43, so that an appropriate dose is introduced into one or several target points 25 or target volumes 20. The dose input is determined 44 in a spatially resolved manner on the basis of the generated particle beam 8 by using the setpoint actuation of the irradiation system 1 and/or of measured values of the irradiation system 1 (especially of the particle beam 8 and/or "direct measurements" 39). In this process, the determination 44 is preferably done for all of the areas of the irradiated body 34, especially (but not necessarily only) for the critical volumes 21 to be protected in the body 34 that is to be irradiated. Subsequently, the dose values that have just been determined (preferably likewise in a spatially resolved manner) are checked 45. Depending on the result of the checking procedure 45, the irradiation method 41 is continued in a different manner. If no signal dose value (especially no warning dose value and/or no maximum dose value) was exceeded, the method is continued 46 without a change. This means that the irradiation is continued in accordance with the original setpoint irradiation 42 (or a setpoint irradiation 47 that has optionally been modified at an earlier point in time). This can also cause the irradiation method 41 to be terminated since, for instance, the dose to be deposited in the tumor 14 has already been reached in accordance with the original setpoint irradiation 42.

In contrast, if a warning dose value has been exceeded, then the planned irradiation (in other words, the original setpoint irradiation 42 or a previously modified plan 47) is changed. The modification here preferably takes place online during the irradiation, a process in which the object to be irradiated is irradiated on the basis of the modified treatment plan. The modification here especially has the goal that, if possible, there is no further rise of radiation in the areas of the body 34 to be irradiated, or only a slight rise, that led to a warning signal being triggered and/or else a relatively high introduced dose (which especially lies above a warning dose value) may have accumulated.

In contrast, if the checking step 45 reveals that a maximum dose has already been reached, then the method 41 is immediately terminated 48. Then a later treatment can preferably only be carried out after approval by the attending physician, whereby the benefit and risk of further treatment has to be weighed on a case-to-case basis.

The method steps and/or device details described in conjunction with FIGS. 1 to 8 can also be employed and implemented on their own and/or in other combinations than the ones explicitly described here.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS 1 irradiation system
2 particle source
3 switching magnet
4 pre-accelerator
5 accelerator ring
6 high-energy beam transportation system
7 irradiation space
8 particle beam
9 gantry
10 axis of the gantry
11 chest
12 lung
13 lung lobe
14 tumor
15 mediastinum
16 aorta
17 spinal column
18 target raster
19 register raster
20 target volume
21 critical tissue area
22 inner area of 20
23 safety margin of 20

24 isodose
25 target point
26 voxel
27 Bragg peak
28 tissue section
29 dose-volume histogram
30 warning value
31 maximum value
32 abscissa
33 ordinate
34 body
35 horizontal scanner
36 vertical scanner
37 energy absorber
38 detector
39 PET
40 control unit
41 irradiation method
42 setpoint irradiation
43 actuation of the irradiation system
44 determination of the dose input
45 checking procedure
46 no change
47 change in the setpoint irradiation
48 termination
49 isoenergy plane
50 inner area of 21
51 safety margin of 21

The invention claimed is:

1. A method for actuating a device for irradiating an object, the object having at least one target volume to be irradiated and at least one volume to be protected, the method comprising:
defining at least one range of permissible values for the volume to be protected;
irradiating the object at least in part with hadron irradiation;
determining, at least one cumulative dose introduced into the volume to be protected during the irradiation of the object;
determining, from the cumulative dose introduced into the volume to be protected when the cumulative dose introduced into the volume to be protected falls outside the range of permissible values, at least one risk potential for the target volume to be irradiated; and
emitting, when the cumulative dose introduced into the volume to be protected falls outside the range of permissible values, at least one dose warning signal including at least one signal value associated with the determined risk potential for the target volume to be irradiated.

2. The method recited in claim 1, wherein the range of permissible values for the volume to be protected is defined according to a dose-volume histogram.

3. The method recited in claim 1, wherein the cumulative dose introduced into the volume to be protected is determined at least partially using from a measured value that has been measured in at least one of the respective volumes and a beam.

4. The method recited in claim 3, wherein the measured value determined in the beam is at least one of a beam position, a beam size, a beam shape, a beam intensity, and a beam energy.

5. The method recited in claim 1, wherein the object being irradiated at least partially moves.

6. The method recited in claim 5, wherein at least one of the target volume to be irradiated and the volume to be protected at least partially moves.

7. The method recited in claim 6, wherein the target volume to be irradiated and the volume to be protected at least partially move relative to each other.

8. The method recited in claim 1, further comprising measuring a position of at least parts of the object to be irradiated.

9. The method recited in claim 8, wherein measuring the position of at least parts of the object to be irradiated uses an imaging method.

10. The method recited in claim 1, wherein the irradiating is carried out in a scanning procedure.

11. The method recited in claim 10, wherein the scanning procedure is a raster scanning procedure.

12. The method recited in claim 11, wherein the at least one target volume to be irradiated comprises at least one target point, and further comprising switching off the at least one target point when the cumulative dose introduced into the volume to be protected falls outside the range of permissible values.

13. The method of claim 12, wherein the switching off of at least one target point is performed only during certain states of motion.

14. The method recited in claim 1, wherein the irradiating is carried out in several partial irradiation procedures;
wherein the several partial irradiation procedures include at least one of several fractions, several re-scanning procedures and a gating method.

15. The method recited in claim 1, wherein determining the cumulative dose introduced into the volume to be protected is performed by an implanted detector in the object.

16. The method recited in claim 1, wherein determining the cumulative dose introduced into the volume to be protected is performed by an external detector not implanted in the object.

17. The method of claim 1, further comprising:
defining a register raster including an array of voxels within the at least one volume to be protected; and
defining a target raster including an array of target point voxels within the at least one target volume to be irradiated;
wherein determining at least one cumulative dose introduced into the volume to be protected comprises determining, for each of one or more voxels in the register raster, a cumulative dose introduced into the voxel during the irradiation of the object,
wherein determining, from the cumulative dose introduced into the volume to be protected, at least one risk potential for the target volume to be irradiated comprises determining, from the cumulative dose value introduced into one or more voxels of the register raster, a risk potential for each of one or more target point voxels at one or more time intervals, and
wherein the at least one signal value associated with the determined risk potential for the target volume to be irradiated includes, for each of at least a portion of the target point voxels for which a risk potential was determined, a signal value associated with the determined risk potential.

18. The method of claim 17, wherein irradiating the object is performed according to an irradiation plan, the method further comprising:
determining, from the at least one dose warning signal, a modified irradiation plan calling for adapted irradiation of each of the one or more target point voxels for which a signal value was included in the at least one dose warning signal.

19. A control unit for actuating an irradiation device for irradiating an object, the object having at least one target volume to be irradiated and at least one volume to be protected, the control unit being configured to, at least at times, carry out a method comprising:

defining at least one range of permissible values for the volume to be protected;

irradiating the object at least in part with hadron irradiation;

determining at least one cumulative dose introduced into the volume to be protected during the irradiation of the object;

determining, from the cumulative dose introduced into the volume to be protected when the cumulative dose introduced into the volume to be protected falls outside the range of permissible values, at least one risk potential for the target volume to be irradiated; and emitting, when the cumulative dose introduced into the volume to be protected falls outside the range of permissible values, at least one dose warning signal including at least one signal value associated with the determined risk potential for the target volume to be irradiated.

20. An irradiation device for irradiating an object, the object having at least one target volume to be irradiated and at least one volume to be protected, comprising:

at least one hadron accelerator; and a control unit being configured to, at least at times, carry out a method comprising:

defining at least one range of permissible values for the volume to be protected;

irradiating the object, at least in part with hadron irradiation;

determining at least one cumulative dose introduced into the volume to be protected during the irradiation of the object;

determining, from the cumulative dose introduced into the volume to be protected when the cumulative dose introduced into the volume to be protected falls outside the range of permissible values, at least one risk potential for the target volume to be irradiated; and emitting, when the cumulative dose introduced into the volume to be protected falls outside the range of permissible values, at least one dose warning signal including at least one signal value associated with the determined risk potential for the target volume to be irradiated.

\* \* \* \* \*